(12) United States Patent
Wangriya (10) Patent No.: US 11,969,714 B2
(45) Date of Patent: Apr. 30, 2024

(54) METHOD AND CATALYST FOR THE PRODUCTION OF 1,3-BUTADIENE FROM ETHANOL

(71) Applicant: SCG CHEMICALS COMPANY LIMITED, Bangkok (TH)

(72) Inventor: Aunchana Wangriya, Pakkred Nonthaburi (TH)

(73) Assignee: SCG CHEMICALS COMPANY LIMITED, Bangsue District Bangkok (TH)

( * ) Notice: Subject to any disclaimer, the term of this patent is extended or adjusted under 35 U.S.C. 154(b) by 279 days.

(21) Appl. No.: 17/430,889

(22) PCT Filed: Feb. 10, 2020

(86) PCT No.: PCT/EP2020/053340
§ 371 (c)(1),
(2) Date: Aug. 13, 2021

(87) PCT Pub. No.: WO2020/165097
PCT Pub. Date: Aug. 20, 2020

(65) Prior Publication Data
US 2022/0080397 A1   Mar. 17, 2022

(30) Foreign Application Priority Data
Feb. 13, 2019 (EP) .................... 19156924

(51) Int. Cl.
*B01J 23/78* (2006.01)
*B01J 21/08* (2006.01)
(Continued)

(52) U.S. Cl.
CPC .............. *B01J 23/78* (2013.01); *B01J 21/08* (2013.01); *B01J 21/10* (2013.01); *B01J 23/002* (2013.01);
(Continued)

(58) Field of Classification Search
CPC ... B01J 23/78; B01J 21/08; B01J 21/10; B01J 23/002; B01J 27/236; B01J 29/40;
(Continued)

(56) References Cited

U.S. PATENT DOCUMENTS

| 7,700,810 B2* | 4/2010 | Kourtakis | ............... C07C 29/34 |
| | | | 568/902.2 |
| 10,669,221 B2* | 6/2020 | Vicente | .................... B01J 23/02 |

(Continued)

FOREIGN PATENT DOCUMENTS

| EP | 2712673 A1 | 4/2014 |
| JP | 2018515339 A | 6/2018 |

(Continued)

OTHER PUBLICATIONS

Marta et al., "Ethanol catalytic condensation over MgAl mixed oxides derived from hydrotalcites", Nov. 2, 2010, vol. 164, No. 1, pp. 436-442.

(Continued)

*Primary Examiner* — Ali Z Fadhel
(74) *Attorney, Agent, or Firm* — COZEN O'CONNOR (57) ABSTRACT

The present invention is concerned with a catalyst for the conversion of ethanol to 1,3-butadiene comprising a component A selected from the list consisting of zeolite, silicon dioxide, aluminium oxide, or any combination thereof; and a component $B_{cat}$ comprising a mixed metal oxide, a catalyst precursor for the preparation of a catalyst for the conversion of ethanol to 1,3-butadiene comprising a component A selected from the list consisting of zeolite, silicon dioxide, aluminium oxide, or any combination thereof; and a component $B_{pre}$ comprising a layered double hydroxide (LDH) as well as a process for the conversion of ethanol to 1,3-butadiene, in which said catalyst is used.

17 Claims, 2 Drawing Sheets

(51) Int. Cl.
  *B01J 21/10*   (2006.01)
  *B01J 23/00*   (2006.01)
  *B01J 27/236*  (2006.01)
  *B01J 29/40*   (2006.01)
  *B01J 35/00*   (2006.01)
  *B01J 35/30*   (2024.01)
  *C07C 1/24*    (2006.01)

(52) U.S. Cl.
  CPC .............. *B01J 27/236* (2013.01); *B01J 29/40* (2013.01); *B01J 35/19* (2024.01); *B01J 35/397* (2024.01); *C07C 1/24* (2013.01); *C07C 2521/06* (2013.01); *C07C 2521/08* (2013.01); *C07C 2521/10* (2013.01); *C07C 2523/755* (2013.01); *C07C 2529/46* (2013.01)

(58) Field of Classification Search
  CPC ...... B01J 35/0006; B01J 35/008; B01J 37/10; B01J 2523/00; B01J 23/02; B01J 35/002; B01J 35/08; B01J 37/035; B01J 37/343; C07C 1/24; C07C 2521/06; C07C 2521/08; C07C 2521/10; C07C 2523/755; C07C 2529/46; C07C 2523/02; C07C 2523/72; C07C 2523/78; C07C 2529/40
  See application file for complete search history.

(56) References Cited

U.S. PATENT DOCUMENTS

2017/0349503 A1* 12/2017 Chinta ................. C07C 1/2076
2018/0264444 A1*  9/2018 O'Hare ................ C09C 1/3054

FOREIGN PATENT DOCUMENTS

| JP | 2018526313 A | 9/2018 |
| WO | 2013125389 A1 | 8/2013 |
| WO | 2016110698 A1 | 7/2016 |
| WO | 2017009664 A1 | 1/2017 |

OTHER PUBLICATIONS

Marta et al., "Consequences of the ironaluminium exchange on the performance of hydrotalcite-derived mixed oxides for ethanol condensation", Dec. 20, 2010, vol. 102, No. 3, pp. 590-599.
International Application No. PCT/EP2020/053340, "International Search Report", dated Apr. 9, 2020, 3 pages.

* cited by examiner

METHOD AND CATALYST FOR THE PRODUCTION OF 1,3-BUTADIENE FROM ETHANOL

This application is a national stage application of PCT/EP2020/053340 filed on Feb. 10, 2020, which claims priority to European App. No. 19156924.3, filed on Feb. 13, 2019, the entirety of which is incorporated herein by reference.

The present invention relates to a catalyst for the conversion of ethanol to 1,3-butadiene comprising a component A and component $B_{cat}$ as well as a catalyst precursor for preparation of such a catalyst comprising component A and component $B_{pre}$. Furthermore, the present invention relates to a process for producing 1,3-butadiene from ethanol as well as the use of said catalyst for the conversion of ethanol to 1,3-butadiene.

BACKGROUND

The demand for butadiene is high as butadiene is used as a monomer in the production of synthetic rubbers, such as butadiene rubber, butadiene-nitrile rubber, butadiene-styrene rubber and the like. Currently, the major amount of the world-wide production of butadiene is produced as a by-product of ethylene production from steam crackers.

In one of the two major industrial processes, butadiene is extracted from the products of oil pyrolysis. In the second method, butadiene is obtained by catalytic dehydrogenation of n-butane and butylenes contained in refining and casing-head gases whereby this method is carried out in one or two steps. However, as the oil prices are on rising, alternative methods to produce butadiene from non-petroleum feedstock become more and more attractive.

One of most potential non-petroleum feedstock is ethanol. The catalytic conversion of ethanol to 1,3-butadiene is well-known. From the 1920s to the early 1960s ethanol was converted to 1,3-butadiene, hydrogen and water at 400 to 450° C. in a one-step process.

However, the mechanism of the conversion of ethanol to 1,3-butadiene is extremely complicated. The main reason for the complexity is that the pathway of the conversion of ethanol to 1,3-butadiene contains multiple reaction steps, which comprise acid, base and redox reactions occurring simultaneously.

The main pathway of ethanol conversion to 1,3-butadiene consists of five key reaction steps, namely, ethanol dehydrogenation, acetaldehyde aldol condensation, acetaldol dehydration, Meerwein-Ponndorf-Verley (MPV) reduction, and crotyl alcohol dehydration. For these reaction pathways a balance between acid-base properties of the catalyst is the key success factor for improving the catalyst activity as well as selectivity and yield of the desired 1,3-butadiene product.

Therefore, there is still the need for finding an improved processes and catalysts for the conversion of ethanol to 1,3-butadiene having improved turn-over numbers, selectivity and yield as well as for a catalyst for the conversion of ethanol to 1,3-butadiene having improved activity and selectivity for said reaction.

Problem to be Solved

Therefore, the object of this invention is to provide a catalyst, which catalyzes the conversion of ethanol to 1,3-butadiene under mild conditions having high catalyst activity, high yield, and high selectivity. It is also an object of the present invention to provide a process for the production of 1,3-butadiene from ethanol having improved selectivity and yield.

SUMMARY OF THE INVENTION

The above-mentioned object is achieved by a catalyst having a specific combination of a component A and a component $B_{cat}$.

Accordingly, the present invention provides a catalyst precursor for the preparation of a catalyst for the conversion of ethanol to 1,3-butadiene comprising a component A selected from a list consisting of zeolite, silicon dioxide, aluminum oxide, or any combination thereof, and a component $B_{pre}$ comprising a layered double hydroxide (LDH).

Furthermore, the present invention provides a catalyst for the conversion of ethanol to 1,3-butadiene comprising a component A selected from a list consisting of zeolite, silicon dioxide, aluminum oxide, or any combination thereof, and a component $B_{cat}$ comprising a mixed metal oxide.

Moreover, the present invention also provides a process for producing 1,3-butadiene comprising contacting an ethanol stream with a catalyst comprising a component A selected from a list consisting of zeolite, silicon dioxide, aluminum oxide, or any combination thereof, and a component $B_{cat}$ comprising a mixed metal oxide.

Finally, the present invention provides the use of the catalyst precursor comprising a component A selected from a list consisting of zeolite, silicon dioxide, aluminum oxide, or any combination thereof, and a component $B_{pre}$ comprising a layered double hydroxide (LDH) for the preparation of a catalyst for the conversion of ethanol to 1,3-butadiene and the use for the a catalyst comprising a component A selected from a list consisting of zeolite, silicon dioxide, aluminum oxide, or any combination thereof, and a component $B_{cat}$ comprising a mixed metal oxide for the conversion of ethanol to 1,3-butadiene.

Definitions

Layered double hydroxides (LDHs) are a class of synthetic or natural two-dimensional nanostructured layered materials with two kinds of metallic cations in the main layers and interlayer domains containing anionic species. A general molecular description of a layered double hydroxide (LDH) is provided by Chemical formula (I):

$$[M^{z+}_{(1-x)}M'^{y+}_{x}(OH)_2]^{a+}A^{n-}_{a/n} \cdot bH_2O \qquad (I)$$

wherein
M and M' are charged metal cations and M is different from M';
z is 1 or 2;
y is 3 or 4;
$A^{n-}$ is the interlayer anion with n>0, preferably n=1-5;
0<x<0.9
b=0-10
a=z(1−x)+xy−2 and is greater than 0

Mixed metal oxide refers to an oxidic form of a mixture of at least two or more metals, a mixture of at least two or more metal oxides, or a combination thereof, without limitation of any physical properties, chemical properties, or preparation method. LDO (layered double oxide) is one preferred embodiment of a mixed metal oxide.

Layered double oxides (LDOs) are derived from layered double hydroxides (LDHs), wherein the layered double hydroxides (LDHs) are heat treated to remove the interlayer water molecules, anions, and hydroxyl groups. Consequently, a structure of the layered double hydroxides (LDHs) at least partially collapsed to form the layered double oxides (LDOs).

The catalyst activity has the unit $[g_{1,3-BD}g_{cat}^{-1}h^{-1}]$ and denotes the quotient of the produced weight of 1,3-butadiene during one hour to the weight of the catalyst.

Weight hourly space velocity (WHSV) as used herein defined the weight of the feed flow per unit weight of the catalyst per hour.

The term time on stream denotes the time period during which the catalyst is in contact with the ethanol feed stream.

The term zeolites as used herein denotes crystalline materials with a structure characterized by a framework of linked tetrahedra, each consisting of four O atoms. This framework contains open cavities in the form of channels and cages which usually are occupied by $H_2O$ molecules and extra-framework cations that are commonly exchangeable.

DESCRIPTION OF THE INVENTION

The present invention provides a catalyst precursor, a catalyst and a process for the production of 1,3-butadiene from ethanol using said catalyst as well as the use of the said catalyst for the production of 1,3-butadiene from ethanol and the use of said catalyst precursor for the preparation of said catalyst.

A. Catalyst Precursor

The present invention provides a catalyst precursor for the preparation of a catalyst for the conversion of ethanol to 1,3-butadiene comprising
i) component A selected from a list consisting of zeolite, silicon dioxide, aluminum oxide, or any combination thereof; and
ii) component $B_{pre}$ comprising a layered double hydroxide (LDH).

Component $B_{pre}$ of the Catalyst Precursor

In an embodiment, the component $B_{pre}$ comprises at least 70% wt of LDH, preferably at least 80% wt of LDH, more preferably at least 90% wt of LDH. In a preferred embodiment, component $B_{pre}$ consists of the layered double hydroxide (LDH).

Preferably, the weight ratio of component A to component $B_{pre}$ is in the range from 1:0.1 to 1:5, more preferably from 1:0.2 to 1:5, even more preferably from 1:0.3 to 1:5. The weight ratio of of component A to component $B_{pre}$ balances the acid-base properties of the catalyst precursor resulting in enhanced yield and selectivity of the conversion of ethanol to 1,3-butadiene with a catalyst derived from the catalyst precursor according to the present invention.

In a preferred embodiment, the LDH comprises a first metal DM and a second metal TM. The first metal DM is at least one monovalent metal cation, one divalent metal cation or a combination thereof. Preferably, the first metal DM is at least one divalent metal cation. Furthermore, the second metal TM is at least one trivalent metal cation, one tetravalent metal cation or a combination thereof. Preferably, the second metal TM is at least one trivalent metal cation.

In one embodiment, the LDH further comprises an interlayer anion. The interlayer anion is selected from a list consisting of $CO_3^{2-}$, $OH^-$, $F^-$, $Cl^-$, $Br^-$, $I^-$, $SO_4^{2-}$, $NO_3^-$ and $PO_4^{3-}$. In a preferred embodiment, the interlayer anion is selected from a list consisting of $CO_3^{2-}$ and $NO_3^-$. In a first most preferred embodiment, the interlayer anion is $CO_3^{2-}$. In a second most preferred embodiment, the interlayer anion is $NO_3^-$.

Preferably, the molar ratio of the first metal DM to the second metal TM is in the range from 1:1 to 10:1, more preferably from 2:1 to 7:1, and most preferably from 2:1 to 5:1.

In a preferred embodiment, the first metal DM is selected from a list consisting of Li, Ca, Mg, Zn, Fe, Co, Cu, Ni, and combinations thereof, preferably from a list consisting of Ca, Mg, Zn, Cu, Ni and combinations thereof, more preferably from a list consisting of Mg, Cu, Ni, Zn and combinations thereof. In a first most preferred embodiment, the first metal DM comprises Mg, preferably consists of Mg. In a second most preferred embodiment, the first metal DM comprises, preferably consists of, a combination of Mg, Cu, and Ni.

In the embodiment where the first metal DM comprises, preferably consists of, a combination of Mg, Cu, and Ni, it is preferred that the molar ratio of Mg:Cu:Ni is in the range of 1-5:0.01-3:0.01-3, preferably 1.5-4.5:0.02-2.5:0.02-2.5 and more preferably 1.8-4:0.02-1.5:0.02-1.5.

In a preferred embodiment, the second metal TM is selected from a list consisting of Al, Ga, In, Y, Fe, Co, Mn, Cr, Ti, V, La, Sn, Zr, and combinations thereof, preferably from a list consisting of Al, Ga, In, Fe, Co, Sn, Zr, and combinations thereof, more preferably from a list consisting of Al, Zr, and combination thereof. In a first most preferred embodiment, the second metal TM comprises, preferably consists of, Al. In a second most preferred embodiment, the second metal TM comprises, preferably consists of, the combination of Al and Zr.

In the embodiment where the second metal TM comprises, preferably consists of the combination of Al and Zr, the molar ratio of Al:Zr is in the range of 0.05-1.5:0.02-1.5, preferably 0.1-1.2:0.05-1.5 and more preferably 0.25-1.15: 0.05-1.15.

In one specific embodiment, the first metal DM comprises, preferably consists of Mg, and the second metal TM comprises, preferably consists of Al, and Zr.

In another specific embodiment, the first metal DM comprises, preferably consists of Mg, Cu, and Ni, and the second metal TM comprises, preferably consists of Al.

It is preferred that the first metal DM and the second metal TM are selected from different metal cations.

In an alternative preferred embodiment, the component $B_{pre}$ further comprises an active metal deposited on the surface of layered double hydroxide (LDH). For example, the deposited LDHs may be obtained by impregnation of the active metal on the LDH. The active metal can be selected from a list consisting of Li, Ca, Zn, Fe, Co, Cu, Ni, Ga, In, Y, Fe, Co, Mn, Cr, Ti, V, La, Sn, Zr, and combinations thereof, preferably from a list consisting of Cu, Ni, Zr, and combinations thereof.

Component A of the Catalyst Precursor

Component A is selected from a list consisting of zeolite, silicon dioxide, aluminum oxide, and combinations thereof. In one preferred embodiment, component A is selected from a list consisting of zeolite, silicon dioxide, and aluminium oxide. In another preferred embodiment, component A is selected from a list consisting of zeolite, silicon dioxide, and combination thereof. In a first most preferred embodiment, component A comprises, preferably at least 80% wt, more preferably at least 90% wt, even more preferably consists of, a silicon dioxide. In a second most preferred embodiment, component A comprises, preferably at least 80% wt, more preferably at least 90% wt, even more preferably consists of, a zeolite.

Silicon Dioxide ($SiO_2$) of Component A of the Catalyst Precursor

In case component A comprises silicon dioxide, the $SiO_2$ according to the present invention may have any shape, size (diameter), and purity. In a preferred embodiment, the silicon dioxide comprises more than 75 wt. % $SiO_2$, preferably more than 85 wt. % $SiO_2$, more preferably more than 95 wt. % $SiO_2$, and most preferably more than 98 wt. % $SiO_2$.

Preferably, the silicon dioxide has a shape of a sphere. The $SiO_2$ sphere can be prepared by any method known in the art. For an example, the $SiO_2$ spheres may be prepared by a modified Stöber process involving ammonia catalysed hydrolysis and condensation of tetraethyl orthosilicate (TEOS) using ethanol as solvent and cetyltrimethylammonium bromide as surfactant porogen, as is well known in the art.

Preferably, the $SiO_2$ sphere is a $SiO_2$ sphere, wherein the $SiO_2$ sphere has an average diameter of between 100 and 1000 nm, preferably of between 200 and 600 nm and more preferably of between 300 and 550 nm.

Zeolite of Component A of the Catalyst Precursor

Preferably, the zeolite of component A of the catalyst precursor of the invention is selected from a list consisting of ZSM-5, X-zeolite, Y-zeolite, USY-zeolite, beta-zeolite, MCM-22, ferrierrite, chabazite, and combinations thereof, more preferably selected from a list consisting of ZSM-5, X-zeolite, Y-zeolite, USY-zeolite, and combinations thereof.

Preferably, the zeolite is present as particles having an average diameter of at least 100 nm, preferably at least 300 nm and more preferably at least 500 nm.

In a preferred embodiment of the invention, the zeolite has a silica to alumina (Si:Al) molar ratio of 1:1 to 5000:1, preferably 15:1 to 2000:1, more preferably 40:1 to 1500:1 and most preferably 250:1 to 1300:1.

Aluminium Oxide of Component A of the Catalyst Precursor

Aluminium oxide is a chemical compound comprising aluminium and oxygen. Preferably, aluminium oxide as used in the present invention comprises, preferably consists of, aluminium-(III)-oxide ($Al_2O_3$).

The aluminium oxide according to the invention may have any shape, sizes (diameters), and purity. In a preferred embodiment, the aluminium oxide comprises more than 75 wt. % $Al_2O_3$, preferably more than 85 wt. % $Al_2O_3$, more preferably more than 95 wt. % $Al_2O_3$, and most preferably more than 98 wt. % $Al_2O_3$.

Preferably, the aluminium oxide according to the present invention comprises, preferably consists of, $Al_2O_3$ having a spherical shape.

In further preferred embodiment of the invention, the aluminium oxide of the present invention is a $Al_2O_3$ sphere. The $Al_2O_3$ sphere can be prepared by any method known in the art.

Structure of the Catalyst Precursor

The catalyst precursor according to the present invention comprises component A and component $B_{pre}$, whereby the component A and component $B_{pre}$ may be structurally combined in several ways. For example, component A may be physically mixed with component $B_{pre}$ or component A may be supported by component $B_{pre}$.

In preferred embodiment of the invention the catalyst precursor has a core-shell structure, whereby core-shell structure means that one component (core) is substantially or totally enclosed by the other component (shell). In an alternative explanation, a core-shell structure is defined by having one component (shell) substantially or totally covering the outer boundary of another component (core). Preferably for the present invention, the core-shell structure has a core which is at least 10%, more preferably at least 20%, even more preferably at least 30%, of its outer surface covered by a shell.

According to a preferred embodiment of the catalyst precursor of the present invention, the core comprises, preferably consists of, component A and the shell comprises, preferably consists of component $B_{pre}$. In another preferred embodiment of the invention, the core consists of component A. In even another preferred embodiment of the invention, the shell consists of component $B_{pre}$.

Preferably, the catalyst precursor of the present invention is present as particles having a primary particle size (average diameter) of between 200 to 3000 nm, preferably between 300 to 2500 nm and more preferably between 400 to 2000 nm measured by Transmission Electron Microscopy (TEM).

B. Catalyst

The present invention provides a catalyst for the conversion of ethanol to 1,3-butadiene comprising
i) component A selected from a list consisting of zeolite, silicon dioxide, aluminum oxide, or any combination thereof; and
ii) component $B_{cat}$ comprising a mixed metal oxide.

Component $B_{cat}$ of the Catalyst

In a preferred embodiment, the component $B_{cat}$ comprises at least 70% wt of mixed metal oxide, preferably at least 80% wt of mixed metal oxide, more preferably at least 90% wt of mixed metal oxide. In a more preferred embodiment, component $B_{cat}$ consists of the mixed metal oxide. In a most preferred embodiment, the mixed metal oxide is a layered double oxide (LDO).

Preferably, the weight ratio of component A to component $B_{cat}$ is in the range from 1:0.05 to 1:2.5, more preferably from 1:0.1 to 1:2.5, even more preferably from 1:0.15 to 1:2.5. The weight ratio of of component A to component $B_{cat}$ balances the acid-base properties of the catalyst resulting in enhanced yield and selectivity of the conversion of ethanol to 1,3-butadiene using the catalyst of the present invention.

In a preferred embodiment, if the mixed-metal oxide comprises, preferably consists of LDO, the LDO comprises a first metal DM and a second metal TM. The first metal DM is at least one monovalent metal cation, one divalent metal cation or a combination thereof. Preferably, the first metal DM is at least one divalent metal cation. Furthermore, the second metal TM is at least one trivalent metal cation, one tetravalent metal cation or a combination thereof. Preferably, the second metal TM is at least one trivalent metal cation.

Preferably, the molar ratio of the first metal DM to the second metal TM is in the range from 1:1 to 10:1, more preferably from 2:1 to 7:1, and most preferably from 2:1 to 5:1. In a preferred embodiment, the LDO has the same molar ratios of the first metal DM to the second metal DM as the LDH of the catalyst precursor, from which the LDO of the catalyst is derived from.

In a preferred embodiment, the first metal DM is selected from a list consisting of Li, Ca, Mg, Zn, Fe, Co, Cu, and Ni and combinations thereof, preferably from a list consisting of Ca, Mg, Zn, Cu, Ni and combinations thereof, more preferably from a list consisting of Mg, Cu, Ni, Zn and combinations thereof. In a first most preferred embodiment, the first metal DM comprises Mg, preferably consists of Mg. In a second most preferred embodiment, the first metal DM comprises, preferably consists of, a combination of Mg, Cu, and Ni.

In the embodiment where the first metal DM comprises, preferably consists of, a combination of Mg, Cu, and Ni, it is preferred that the molar ratio of Mg:Cu:Ni is in the range of 1-5:0.01-3:0.01-3, preferably 1.5-4.5:0.02-2.5:0.02-2.5 and more preferably 1.8-4:0.02-1.5:0.02-1.5.

In a preferred embodiment, the second metal TM is selected from a list consisting of Al, Ga, In, Y, Fe, Co, Mn, Cr, Ti, V, La, Sn, Zr, and combinations thereof, preferably from a list consisting of Al, Ga, In, Fe, Co, Sn, Zr, and combinations thereof, more preferably from a list consisting of Al, Zr, and combination thereof. In a first most preferred embodiment, the second metal TM comprises, preferably consists of, Al. In a second most preferred embodiment, the second metal TM comprises, preferably consists of, the combination of Al and Zr.

In the embodiment where the second metal TM comprises, preferably consists of the combination of Al and Zr, the molar ratio of Al:Zr is in the range of 0.05-1.5:0.02-1.5, preferably 0.1-1.2:0.05-1.5 and more preferably 0.25-1.15: 0.05-1.15.

In one specific embodiment, the first metal DM comprises, preferably consist of Mg, and the second metal TM comprises, preferably consists of Al, and Zr.

In another specific embodiment, the first metal DM comprises, preferably consist of Mg, Cu, and Ni, and the second metal TM comprises, preferably consists of Al.

It is preferred that the first metal DM and the second metal TM are selected from different metal cations.

In an alternative preferred embodiment, the component $B_{cat}$ further comprises an active metal deposited on the surface of a layered double hydroxide (LDO). For example, the deposited LDOs may be obtained by impregnation of the active metal on the LDO. The active metal is selected from a list consisting of Li, Ca, Zn, Fe, Co, Cu, Ni, Ga, In, Y, Fe, Co, Mn, Cr, Ti, V, La, Sn, Zr, and combinations thereof, preferably from a list consisting of Cu, Ni, Zr, and combinations thereof.

In a preferred embodiment, the LDO of the catalyst has the same combination of first metal DM and second metal TM as found in the LDH of the catalyst precursor, from which the LDO of the catalyst is derived from.

Component A of the Catalyst

Component A is selected from a list consisting of zeolite, silicon dioxide, aluminium oxide, and combinations thereof. In one preferred embodiment, component A is selected from a list consisting of zeolite, silicon dioxide, and aluminium oxide. In another preferred embodiment, component A is selected from a list consisting of zeolite, silicon dioxide, and combinations thereof. In a first most preferred embodiment, component A comprises, preferably at least 80% wt, more preferably at least 90% wt, even more preferably consists of, a silicon dioxide. In a second most preferred embodiment, component A comprises, preferably at least 80% wt, more preferably at least 90% wt, even more preferably consists of, a zeolite. Preferably, component A of the catalyst is identical to component A of the catalyst precursor.

Silicon Dioxide ($SiO_2$) of Component A of the Catalyst

In case component A comprises silicon dioxide, the $SiO_2$ according to the present invention may have any shape, size (diameter), and purity. In a preferred embodiment, the silicon dioxide comprises more than 75 wt. % $SiO_2$, preferably more than 85 wt. % $SiO_2$, more preferably more than 95 wt. % $SiO_2$, and most preferably more than 98 wt. % $SiO_2$.

Preferably, the silicon dioxide has a shape of a sphere. The $SiO_2$ sphere can be prepared by any method known in the art. For an example, the $SiO_2$ spheres may be prepared by a modified Stöber process involving ammonia catalysed hydrolysis and condensation of tetraethyl orthosilicate (TEOS) using ethanol as solvent and cetyltrimethylammonium bromide as surfactant porogen, as is well known in the art.

Preferably, the $SiO_2$ sphere is a $SiO_2$ sphere, wherein the $SiO_2$ sphere has an average diameter of between 100 and 1000 nm, preferably of between 200 and 600 nm and more preferably of between 300 and 550 nm.

Zeolite of Component A of the Catalyst

Preferably, the zeolite of component A of the catalyst of the invention is selected from a list consisting of ZSM-5, X-zeolite, Y-zeolite, USY-zeolite, beta-zeolite, MCM-22, ferrierrite, chabazite, and combinations thereof, more preferably selected from a list consisting of ZSM-5, X-zeolite, Y-zeolite, USY-zeolite, and combinations thereof.

Preferably, the zeolite is present as particles having an average diameter of at least 100 nm, preferably at least 300 nm and more preferably at least 500 nm.

In a preferred embodiment of the invention, the zeolite has a silica to alumina (Si:Al) molar ratio of 1:1 to 5000:1, preferably 15:1:1 to 2000:1, more preferably 40:1 to 1500:1 and most preferably 250:1 to 1300:1.

Aluminium Oxide of Component A of the Catalyst

Aluminium oxide is a chemical compound comprising aluminium and oxygen. Preferably, aluminium oxide as used in the present invention comprises, preferably consists of, aluminium-(III)-oxide ($Al_2O_3$).

The aluminium oxide according to the invention may have any shape, sizes (diameters), and purity. In a preferred embodiment, the aluminium oxide comprises more than 75 wt. % $Al_2O_3$, preferably more than 85 wt. % $Al_2O_3$, more preferably more than 95 wt. % $Al_2O_3$, and most preferably more than 98 wt. % $Al_2O_3$.

Preferably, the aluminium oxide according to the present invention comprises, preferably consists of, $Al_2O_3$ having a spherical shape.

In further preferred embodiment of the invention, the aluminium oxide of the present invention is a $Al_2O_3$ sphere. The $Al_2O_3$ sphere can be prepared by any method known in the art.

Structure of the Catalyst

The catalyst according to the present invention comprises component A and component $B_{cat}$, whereby the component A and component $B_{cat}$ may be structurally combined in several ways. For example, component A may be physically mixed with component $B_{cat}$ or component A may be supported by component $B_{cat}$.

In preferred embodiment of the invention, the catalyst has a core-shell structure, whereby core-shell structure means that one component (core) is enclosed by the other component (shell). In an alternative explanation, a core-shell structure is defined by having one component (shell) substantially or totally covering the outer boundary of another component (core). Preferably for the present invention, the core-shell structure has a core which is at least 10%, more preferably at least 20%, even more preferably at least 30%, of its outer surface covered by a shell.

According to a preferred embodiment of the catalyst of the present invention, the core comprises, preferably consists of, component A and the shell comprises, preferably consists of component $B_{cat}$. In another preferred embodiment of the invention, the core consists of component A. In even another preferred embodiment of the invention, the shell consists of component $B_{cat}$.

Preferably, the catalyst of the present invention is present as particles having a primary particle size (average diameter) of between 200 to 3000 nm, preferably between 300 to 2500 nm and more preferably between 400 to 2000 nm measured by Transmission Electron Microscopy (TEM).

C. Preparation of the Catalyst Precursor

The catalyst precursor of the present invention can be prepared by a co-precipitation method to form the preferred core-shell structure. The co-precipitation method comprises the steps of:
a) Preparing a suspension by contacting component A with
   i) a solution comprising an anion salt, ii) an aqueous metal precursor solution containing metal ions, preferably metal ions DM and TM, of component $B_{pre}$ and iii) a base,
b) Filtrating the solid compound off the suspension resulting from step a) and washing the solid compound with deionized water and obtaining a wet cake, and
c) Drying the wet cake of the solid compound resulting from step b).

For example, to obtain a core-shell structure, in which the core comprises component A, and the shell comprises component $B_{pre}$ the following process can be used. Component A is dispersed as a powder in deionized water using ultrasound treatment. Subsequently, the anion salt, $Na_2CO_3$, is added under further treatment by ultrasound. Then an aqueous metal precursor solution containing metal ions DM and TM of component $B_{pre}$ is added to the mixture of deionized water, component A and $Na_2CO_3$ under vigorous stirring while maintaining pH of the mixture at pH 10 by addition of NaOH at a temperature of approximately 25° C. The obtained suspension is then filtrated using vacuum filtration and the obtained solid compound is washed with deionized water until pH 7 is achieved. The solid compound will then be present in form of a wet cake. The wet cake of the solid compound is then dried overnight under heating at a temperature of at least 80° C. to obtain a dried powder of the catalyst precursor according to the present invention having a core-shell structure.

D. Preparation of the Catalyst

The core-shell structure of the catalyst according to the present invention can be prepared by a method including homogeneous co-precipitation. In a preferred embodiment LDH is precipitated on component A. Hence, the first step of the process for the preparation for the catalyst according to the present invention might comprise the preparation of a catalyst precursor according to the present invention.

Thus, preferably, the catalyst according to the present invention is preferably prepared by preparation of the catalyst precursor and an additional calcining step. Hence, the mixed metal oxide, preferably LDO, as found in component $B_{cat}$ of the catalyst is preferably derived by calcining the LDH as found in component $B_{pre}$ of the catalyst precursor.

Hence, the preparation method for the catalyst comprises the co-precipitation method comprising step a) to step c) for the catalyst precursor as described in the present invention, whereas component $B_{pre}$ is component $B_{cat}$ in the catalyst, further comprising a calcination step d), which is preferably performed after step c).

In a preferred embodiment the calcination step d) of the preparation method of the catalyst is performed at a temperature between 300 and 700° C., preferably 400 and 600° C. and more preferably 450 and 550° C.

In an even more preferred embodiment of the invention the calcination step d) of the preparation method of the catalyst is performed for at least 1 h, preferably at least 2 h and more preferably at least 3 h. Preferably, the calcination step d) is performed for 1 to 6 h, more preferably for 2 to 5.5 h.

Most preferably, the calcination step d) is performed at a temperature between 450 and 550° C. for at least 2 h.

The core-shell structure of the catalyst according to the invention may be evidenced by Scanning Electron Microscopy (SEM), Transmission Electron Microscopy (TEM), and X-ray powder diffraction (XRD).

It has been found that the core-shell structure of the catalyst of the present invention is composed of layers of sequentially-exposed active components.

In an embodiment, the preparation process for the catalyst according to the present invention may further comprise a step e) of forming the catalyst powder into a shape suitable for a commercial reactor. The step e) can be performed before or after step d). Preferably, the step e) is performed before step d) and after step c).

Shapes suitable for a commercial reactor may include pellets, extrudates, spheres, and the like. Sufficient binder materials may be further added to the ethanol conversion catalyst composition to facilitate forming of the catalyst. Providing the catalyst in a specific shape allows a facilitated use thereof.

In an embodiment, the catalyst according to the present invention is a particle with a specific surface area of at least 50 $m^2/g$, preferably at least 100 $m^2/g$, more preferably at least 150 $m^2/g$, and even more preferably at least 200 $m^2/g$. Preferably, the specific surface are of the catalyst according to the present invention is lower than 700 $m^2/g$, more preferably lower than 600 $m^2/g$ and most preferably lower than 500 $m^2/g$. The specific surface area is measured after the calcination by using Brunauer-Emmett-Teller (BET) surface area analysis.

In an especially preferred embodiment of the invention, the catalyst has a core-shell structure, whereas the core comprises, preferably consists of component A, and the shell comprises, preferably consists of, component $B_{cat}$, the catalyst having a specific surface area of at least 50 $m^2/g$ and lower than 700 $m^2/g$, whereby preferably the specific surface area is measured after the calcination.

In a preferred embodiment the core-shell ethanol conversion catalyst has a thickness of shell larger than 5 nm, preferably larger than 10 nm and more preferably of larger than 20 nm, preferably the thickness is measured after the calcination.

E. Conversion of Ethanol to 1,3-butadiene

The process for producing 1,3-butadiene comprises contacting an ethanol stream with the catalyst according to the invention, whereby the process can be operated under a wide range of operating conditions. However, specific ranges of operating conditions can result in better 1,3-butadiene production efficiency.

In a preferred embodiment, the process is carried out at a temperature in the range from 250-500° C., preferably in the range from 300-500° C., and more preferably in the range from 320-450° C.

In another preferred embodiment, the process for producing 1,3-butadiene from ethanol is carried out at atmospheric pressure.

The contact time needed to obtain a desirable yield of 1,3-butadiene product depends upon several factors such operating temperature, operating pressure, and catalyst activity.

In a preferred embodiment, the process is carried out at a weight hourly space velocity (WHSV) in the range from 0.1 to 40 $h^{-1}$, preferably in the range from 0.3 to 20 $h^{-1}$, and more preferably in the range from 0.5 to 10 $h^{-1}$.

The process can be conducted in batchwise or a continuously. For commercial scale, it is favorable that the process is operated continuously using a fixed bed. Particularly preferred, the process is carried out continuously in a one-step process and/or a single stage reactor.

The catalyst activity of the catalyst used in the process for producing 1,3 butadiene preferably is at least 0.1 $g_{1,3-BD}g_{cat}^{-1}h^{-1}$, more preferably 0.2 $g_{1,3-BD}g_{cat}^{-1}h^{-1}$, and most preferably 0.3 $g_{1,3-BD}g_{cat}^{-1}h^{-1}$. Moreover, the catalyst activity of the catalyst used in the process for producing 1,3 butadiene preferably is not more than 10 $g_{1,3-BD}g_{cat}^{-1}h^{-1}$.

The product stream obtained by the process for producing 1,3 butadiene preferably comprises at least 12 wt % 1,3 butadiene, more preferably at least 15 wt % 1,3 butadiene, and most preferably at least 20 wt % 1,3 butadiene. Moreover, the product stream obtained by the process for producing 1,3 butadiene preferably may comprise not more than 95 wt % 1,3 butadiene.

The product stream obtained by the process for producing 1,3 butadiene preferably comprises not more than 20 wt % ethylene, more preferably not more than 15 wt % ethylene. Moreover, the product stream obtained by the process for producing 1,3 butadiene preferably may comprise at least 0.1 wt % ethylene.

In a specifically preferred embodiment, the ethanol conversion to 1,3-butadiene process is carried out by contacting an ethanol feed stream with the catalyst according to the present invention under reaction conditions having a temperature of 320-400° C., atmospheric pressure, and a WHSV 1.55 $h^{-1}$.

The ethanol feed stream according to the process of the present invention may be in any purity. In a preferred embodiment, the ethanol feed stream comprises more than 75 wt. % ethanol, preferably more than 85 wt. % ethanol, more preferably more than 95 wt. % ethanol, and most preferably more than 98 wt. % ethanol.

After contacting the catalyst of the present invention with the ethanol feed stream under the discussed operating conditions, some poisonous substances and coke may deposit on the surface of the catalyst. This normally affects activity of the catalyst to gradually decrease over time. A suitable regeneration can be performed on the used catalyst to recover at least some of its activity.

Figure 1:
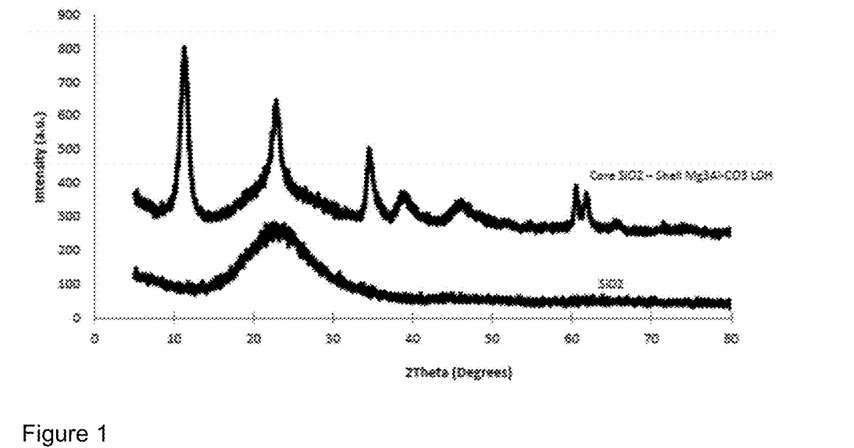
FIG. 1: XRD patterns of pure $SiO_2$ and the core-shell $SiO_2$—$Mg_3Al$—$CO_3$ LDH (IE1)
Figure 5:
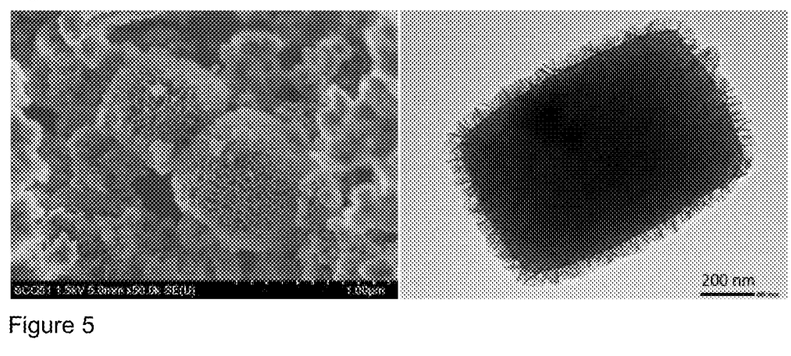

FIG. 5: SEM and TEM images of the core-shell Zeolite ZA—$Mg_3Al$—LDH (IE2) with Zeolite ZA as core FIG. 1 shows the XRD patterns of pure $SiO_2$ and the core-shell $SiO_2$—$Mg_3Al$—$CO_3$ LDH. By this image it can be shown that the core-shell $SiO_2$—$Mg_3Al$—$CO_3$ LDH samples were successfully synthesized since characteristic peaks of $Mg_3Al$—$CO_3$ LDH can be observed, which are the sharp and intense (003), (006), (009), (015), (018), (110), and (113) reflections at $2\theta$=11.50, 22.90, 34.74, 39.13, 46.28, 60.46, and 61.80. $SiO_2$ can be found at $2\theta$=22.6.

Figure 2:
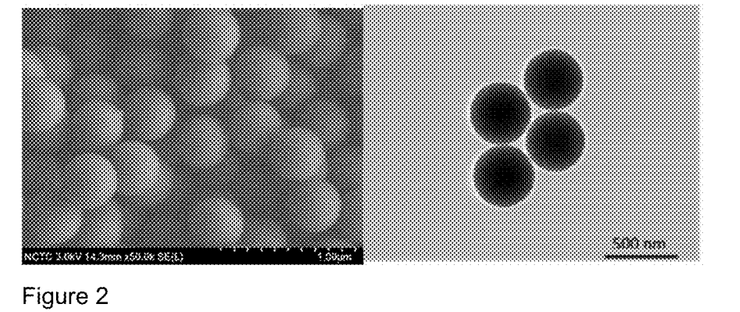
FIG. 2: SEM and TEM images of $SiO_2$ spheres
Figure 4:
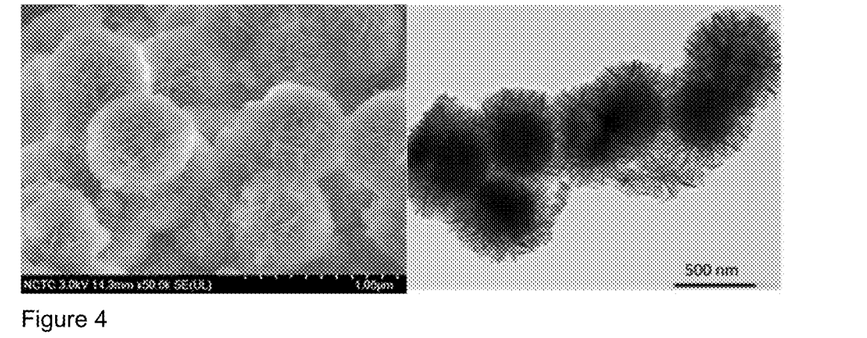
FIG. 4: SEM and TEM images of the core-shell $SiO_2$—$Mg_3Al$—LDH with $SiO_2$ spheres as core (IE1)

FIG. 4 shows the SEM and TEM images of the core-shell $SiO_2$—$Mg_3Al$—LDH with core $SiO_2$ spheres which shows the formation of a LDH shell over silica sphere cores which is shown in FIG. 2.

Figure 3:
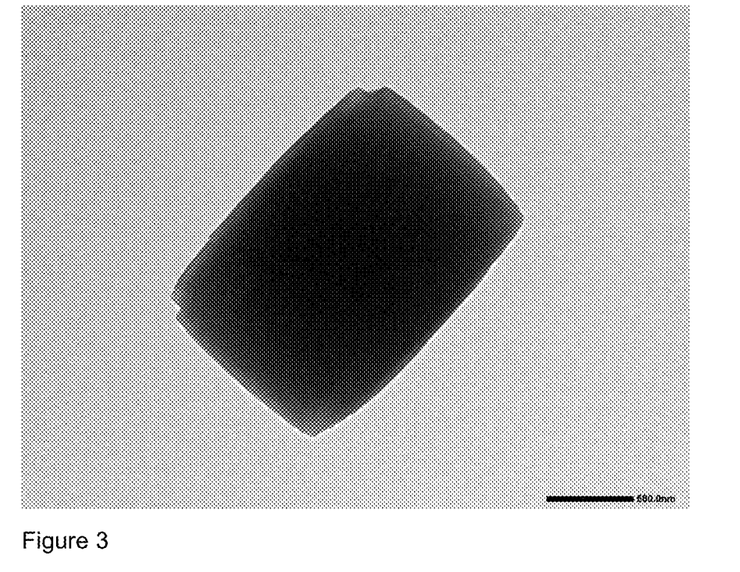
FIG. 3: TEM image of Zeolite ZA

FIG. 5 shows the SEM and TEM images of the core-shell Zeolite ZA—$Mg_3Al$—LDH with core Zeolite ZA which shows the formation of a LDH shell over Zeolite ZA cores which is shown in FIG. 3.

Measurement Methods a) The X-ray powder diffraction (XRD)

The X-ray powder diffraction (XRD) patterns of a sample were identified using a X-ray powder diffractometer (Rikagu TTRAX III) with a monochromator and Cu-K$\alpha$ radiation at $\lambda$=0.15405 nm. The 2-theta was ranged from 5° to 80° with the scan speed of 3°/min and the scan step of 0.02°.

b) Scanning Electron Microscopy (SEM)

Scanning Electron Microscopy (SEM) analysis was performed on a JEOL JSM 6610 scanning electron microscope. Particles were dispersed in water and cast onto a clean silica wafer. Energy dispersive X-ray spectroscopy (EDX), also carried out on this instrument, was used to determine the relative quantities of constituent elements on the surface of the sample.

c) Transmission Electron Microscopy (TEM)

Transmission Electron Microscopy (TEM) analysis was performed on a JEOL 2100 Plus microscope with an accelerating voltage of 200 kV. Particles were dispersed in water or ethanol using sonication and subsequently cast onto copper grids coated with carbon film and left to dry.

d) Gas Chromatography (GC)

The gaseous products were analysed by gas chromatography (Agilent Technologies 6890 Network GC system) using a HP-PLOT $Al_2O_3$ column (50 m×0.32 mm ID and 20 μm film thickness) equipped with a flame ionization detector (FID) to determine hydrocarbon gases. The GC operating conditions were set as followed:

Initial temperature: 40° C. (10 min holding time)
Ramp 1:
Heating rate: 10° C./min
Final temperature: 120° C. and 10 min holding time
Ramp 2:
Heating rate: 5° C./min
Final temperature: 180° C. (10 min holding time)

e) Gas Chromatography-Mass Spectrometry, Time of Flight (GC-TOF)

The liquid products were analysed using a gas chromatograph equipped with a mass spectrometer of a time of flight type (GC×GC-TOF/MS), Agilent 7890. Helium was used as the carrier gas, and nitrogen was used in the cooling system. The conditions were set as followed:

Initial temperature: 40° C. (2 min holding time)
Heating rate: 2.5° C./min
Final temperature: 250° C. (5 min holding time)
Split ratio: 1:25

EXPERIMENTAL PART

Materials

ZA is a ZSM-5 zeolite having a Si:Al ratio of 250-700.
ZB is a ZSM-5 zeolite-having a Si:Al ratio of 800-1300.

Comparative Example 1 (CE1): $Mg_3Al$—$CO_3$ LDH (Chemical Formula: $Mg_{0.75}Al_{0.25}(OH)_2(CO_3)_{0.125}$)

$Mg_3Al$—$CO_3$ LDH was synthesized by adding 700 ml of an aqueous metal precursor solution containing 1.575 mol $Mg(NO_3)_2 \cdot 6H_2O$ and 0.525 mol $Al(NO_3)_3 \cdot 9H_2O$ to 700 ml of a solution of 0.315 mol $Na_2CO_3$. The pH of the resulting solution was controlled at pH 10 by dropwise adding of 4 M NaOH under vigorous stirring. Subsequently, the obtained solution was aged for 3 h at a temperature of approximately 25° C. After aging, the precipitated solid compound was filtered off the solution and washed with deionized water until a pH=7 of the filtrate was reached. Finally, the wet cake of solid compound was dried in an oven at 110° C. overnight. Comparative Example 1 represents an example having no core, but only a shell of $Mg_3Al$—$CO_3$ LDH Comparative Example 2 (CE2): $Cu_{0.5}Ni_{0.2}Mg_{2.3}Al$—$CO_3$ LDH (Chemical Formula: $Cu_{0.125}Ni_{0.05}Mg_{0.575}Al_{0.25}(OH)_2(CO_3)_{0.125}$)

$Cu_{0.5}Ni_{0.2}Mg_{2.3}Al$—$CO_3$ LDH was synthesized by adding 700 ml of an aqueous metal precursor solution containing 1.208 mol $Mg(NO_3)_2 \cdot 6H_2O$, 0.2625 mol $Cu(NO_3)_2 \cdot 6H_2O$, 0.105 mol $Ni(NO_3)_2 \cdot 6H_2O$ and 0.525 mol $Al(NO_3)_3 \cdot 9H_2O$ to 700 ml of a solution of 0.315 mol $Na_2CO_3$. The pH of the resulting solution was controlled at pH 10 by dropwise adding of 4 M NaOH under vigorous stirring. Subsequently, the obtained solution was aged for 3 h at a temperature of approximately 25° C. After aging the precipitated solid compound was filtered off the solution and washed with deionized water until a pH=7 of the filtrate was reached. Finally, the wet cake of solid compound was dried in an oven at 80° C. overnight. Comparative Example 2 represents an example having no core, but only a shell of $Cu_{0.5}Ni_{0.2}Mg_{2.3}Al$—$CO_3$ LDH.

Inventive Example 1 (IE1): Core $SiO_2$—Shell $Mg_3Al$—$CO_3$ LDH (Chemical Formula: $Mg_{0.75}Al_{0.25}(OH)_2(CO_3)_{0.125}$)

Silica having a spherical shape with 500 nm particle diameter was used as the core for the synthesis of IE1. IE1 was synthesized by a co-precipitation method as explained in the following: 5 g of silica having the shape of a sphere was dispersed in 1000 ml deionized water using an ultrasound treatment for 30 min. Subsequently, 27 mmol $Na_2CO_3$ were added and further treated by ultrasound for 5 min. Then 1000 ml of an aqueous metal precursor solution containing 81 mmol $Mg(NO_3)_2 \cdot 6H_2O$ and 27 mmol $Al(NO_3)_3 \cdot 9H_2O$ ml were added to the mixture of deionized water, silica and $Na_2CO_3$ under vigorous stirring resulting in a suspension. The pH of the suspension was controlled at pH 10 by dropwise adding of 1 M NaOH. After aging for 120 min under stirring at a temperature of approximately 25° C., the obtained solid compound was filtered off the suspension using vacuum filtration and washed using deionized water until a pH=7 of the filtrate was reached. Finally, the wet cake of the solid compound was dried in an oven at 110° C. overnight.

Inventive Example 2 (IE2): Core Zeolite ZA—Shell $Mg_3Al$—$CO_3$ LDH (Chemical Formula: $Mg_{0.75}Al_{0.25}(OH)_2(CO_3)_{0.125}$)

Also IE2 was synthesized using a co-precipitation method: 5 g of zeolite ZA were dispersed in 1000 ml deionized water using an ultrasound treatment for 30 min. Subsequently, 27 mmol $Na_2CO_3$ were added and further treated by ultrasound for 5 min. Then the 1000 ml of an aqueous metal precursor solution containing 81 mmol $Mg(NO_3)_2 \cdot 6H_2O$ and 27 mmol $Al(NO_3)_3 \cdot 9H_2O$ ml were added to the mixture of deionized water, zeolite ZA and $Na_2CO_3$ under vigorous stirring resulting in a suspension. The pH of the suspension was controlled at pH 10 by dropwise adding of 1 M NaOH. After aging for 120 min under stirring at a temperature of approximately 25° C., the obtained solid compound was filtered off the suspension using vacuum filtration and washed using deionized water until pH=7 of the filtrate was reached. Finally, the wet cake of the solid compound was dried in an oven at 110° C. overnight.

Inventive Example 3 (IE3): Core $SiO_2$—Shell $Mg_3Al_{0.9}Zr_{0.1}$—$CO_3$ LDH (Chemical Formula $Mg_{0.75}Al_{0.225}Zr_{0.025}(OH)_2(CO_3)_{0.125}$)

Silica having a spherical shape with 500 nm particle diameter was used as the core for the synthesis of IE3. IE3 was again synthesized by a co-precipitation method: 5 g of silica having the shape of a sphere were dispersed in 1000 ml deionized water using an ultrasound treatment for 30 min. Subsequently, 27 mmol $Na_2CO_3$ were added and further treated by ultrasound for 5 min. Then 1000 ml of an aqueous metal precursor solution containing 81 mmol $Mg(NO_3)_2 \cdot 6H_2O$, 24.3 mmol $Al(NO_3)_3 \cdot 9H_2O$ and 2.7 mmol $ZrN_2O_7 \cdot 9H_2O$ were added to the mixture of deionized water, silica and $Na_2CO_3$ under vigorous stirring resulting in a suspension. The pH of the suspension was controlled at pH 10 by dropwise adding of 1 M NaOH. After aging for 120 min under stirring at a temperature of approximately 25° C., the obtained solid compound was filtered off the suspension using vacuum filtration and washed using deionized water until pH=7 of the filtrate was reached. Finally, the wet cake of the solid compound was dried in an oven at 80° C. overnight.

Inventive Example 4 (IE4)—Core Zeolite ZB—Shell $Cu_{0.5}Ni_{0.2}Mg_{2.3}Al$—$CO_3$ LDH (Chemical Formula: $Cu_{0.125}Ni_{0.05}Mg_{0.575}Al_{0.25}(OH)_2(CO_3)_{0.125}$)

IE4 was also synthesized by the co-precipitation method: 5 g of zeolite ZB were dispersed in 1000 ml deionized water using an ultrasound treatment for 30 min. Subsequently, 27 mmol Na₂CO₃ and further treated by ultrasound for 5 min. Then 1000 ml of an aqueous metal precursor solution containing 13.5 mmol Cu(NO₃)₂•6H₂O, 5.4 mmol Ni(NO₃)₂•6H₂O, 62.1 mmol Mg(NO₃)₂•6H₂O and 27 mmol Al(NO₃)₃•9H₂O were added the mixture of deionized water, zeolite ZB and Na₂CO₃ under vigorous stirring resulting in a suspension. The pH of the suspension was controlled at pH 10 by dropwise adding of 1 M NaOH. After aging for 120 min under stirring at a temperature of approximately 25° C., the obtained solid compound was filtered off the suspension using vacuum filtration and washed using deionized water until pH=7 of the filtrate was reached. Finally, the wet cake of the solid compound was dried in an oven at 80° C. overnight.

Conversion of Ethanol to 1,3-butadiene

The catalysts precursor as produced in CE1 to CE2 and IE1 to IE4 were calcined at a temperature of 500° C. transforming the LDHs of the catalyst precursor to LDOs and subsequently contacted with an ethanol feed stream at a temperature of 350° C., under atmospheric pressure, and at a weight hourly space velocity (WHSV) of 1.55 h⁻¹. The reaction was carried out for 3 h (time on stream). The products obtained were divided in liquid and gaseous products. The liquid products were analyzed using a gas chromatograph equipped with a mass spectrometer of a time of flight type (GC×GC-TOF/MS). The gaseous products were analyzed by gas chromatography (Agilent Technologies 6890 Network GC system) using a HP-PLOT Al₂O₃ column (50 m×0.32 mm ID and 20 μm film thickness) equipped with a flame ionization detector (FID) to determine hydrocarbon gases.

The results of the conversion reaction of ethanol to 1,3 butadiene at a time on stream for 3 h are displayed in Table 1.

The inventive catalysts according to IE1 to IE4 comprise both a component A and a component $B_{cat}$. It is found that their 1,3-butadiene yields and the catalyst activities are significantly increased in comparison to CE1 and CE2.

The invention claimed is:

1. A catalyst for the conversion of ethanol to 1,3-butadiene comprising
    i) component A, which is selected from a list consisting of zeolite, silicon dioxide, aluminum oxide, or any combination thereof; and
    ii) component $B_{cat}$ comprising a mixed metal oxide; wherein the mixed metal oxide is a layered double oxide, wherein the layered double oxide comprises a first metal DM and a second metal TM, characterized in that the first metal DM comprises a combination of Mg, Cu, and Ni.

2. The catalyst according to claim 1, wherein the weight ratio of component A to component $B_{cat}$ is in the range from 1:0.05 to 1:2.5.

3. The catalyst according to claim 1, wherein the catalyst has a core-shell structure, wherein the core of the core-shell structure comprises component A and the shell of the core-shell-structure comprises component $B_{cat}$.

4. The catalyst according to claim 1, wherein the second metal TM is selected from a list consisting of Al, Ga, In, Y, Fe, Co, Mn, Cr, Ti, V, La, Sn, Zr, and combinations thereof.

5. The catalyst according to claim 1, wherein component A is a zeolite selected from the group consisting of ZSM-5, X-zeolite, Y-zeolite, USY-zeolite, beta-zeolite, MCM-22, ferrierrite, chabazite, and combinations thereof.

6. The catalyst according to claim 5, wherein the zeolite has a molar ratio of Si to Al in the range from 1:1 to 5000:1.

7. The catalyst according to claim 1, wherein the molar ratio of Mg:Cu:Ni is in the range of 1-5: 0.01-3: 0.01-3.

TABLE 1

| | | | Conditions | | Results | | |
|---|---|---|---|---|---|---|---|
| | | | | | Time on Stream: 3 h | | |
| No. | Component A | Component $B_{cat}$ | Temperature [° C.] | WHSV [h⁻¹] | 1,3-butadiene yield [% wt] | Ethylene yield [% wt] | Catalyst Activity [$g_{1,3\text{-}BD}\, g_{cat}^{-1}\, h^{-1}$] |
| CE1 | — | Mg₃Al | 350 | 1.55 | 12.4 | 20.1 | 0.19 |
| IE1 | SiO₂ | Mg₃Al | 350 | 1.55 | 20.3 | 12.4 | 0.32 |
| IE2 | Zeolite ZA | Mg₃Al | 350 | 1.55 | 35.8 | 7.5 | 0.56 |
| IE3 | SiO₂ | Mg₃Al₀.₉Zr₀.₁ | 350 | 1.55 | 37.9 | 9.5 | 0.59 |
| CE2 | — | Cu₀.₅Ni₀.₂Mg₂.₃Al | 350 | 1.55 | 15.3 | 15.4 | 0.24 |
| IE4 | Zeolite ZB | Cu₀.₅Ni₀.₂Mg₂.₃Al | 350 | 1.55 | 38.2 | 13.4 | 0.59 |

In Table 1 the % 1,3-butadiene yield and the catalyst activity after performing the reaction are the key parameters to indicate the catalyst performance.

The catalyst of the CE1 consists of Mg and Al and does not contain component A (i.e. any core). While this catalyst at least converts ethanol to 1,3-butadiene, it is found that the 1,3 butadiene yield and the catalyst activity are lowest for CE1 in comparison to CE2 and IE1 to IE 4. Hence, the catalyst composition of CE1 is used as baseline for all remaining examples CE2 and IE1 to IE4. The catalyst of CE2 has improved performance compared to the catalyst of CE1. The LDH of CE2 comprises Cu and Ni together with Mg and Al. Furthermore, the catalyst of CE2 does not contain component A (i.e. any core). The 1,3 butadiene yield and the catalyst activity are slightly increased in comparison to CE1.

8. A process for producing 1,3-butadiene comprising contacting an ethanol stream with a catalyst according to claim 1.

9. Use of a catalyst according to claim 1 for the conversion of ethanol to 1,3-butadiene.

10. A catalyst precursor for the preparation of a catalyst for the conversion of ethanol to 1,3-butadiene comprising
    i) component A, which is selected from a list consisting of zeolite, silicon dioxide, aluminum oxide, or any combination thereof; and
    ii) component $B_{pre}$ comprising a layered double hydroxide
    wherein the layered double hydroxide comprises a first metal DM and a second metal TM, characterized in that the first metal DM comprises a combination of Mg, Cu, and Ni.

11. The catalyst precursor according to claim 10, wherein the weight ratio of component A to component $B_{pre}$ is in the range from 1:0.1 to 1:5.

12. The catalyst precursor according to claim 10, wherein the catalyst precursor has a core-shell structure, wherein the core of the core shell structure comprises component A and the shell of the core-shell-structure comprises component $B_{pre}$.

13. The catalyst precursor according to claim 10, wherein the second metal TM is selected from a list consisting of Al, Ga, In, Y, Fe, Co, Mn, Cr, Ti, V, La, Sn, Zr, and combinations thereof.

14. The catalyst precursor according to claim 10, wherein component A is a zeolite selected from the group consisting of ZSM-5, X-zeolite, Y-zeolite, USY-zeolite, beta-zeolite, MCM-22, ferrierrite, chabazite, and combinations thereof.

15. The catalyst precursor according to claim 14, wherein the zeolite has a molar ratio of Si to Al in the range from 1:1 to 5000:1.

16. Use of a catalyst precursor according to claim 10 for the preparation of a catalyst for the conversion of ethanol to 1,3-butadiene.

17. The catalyst precursor according to claim 10, wherein the molar ratio of Mg:Cu:Ni is in the range of 1-5: 0.01-3: 0.01-3.

* * * * *